(12) United States Patent
Iyer et al.

(10) Patent No.: US 10,956,792 B2
(45) Date of Patent: Mar. 23, 2021

(54) METHODS AND APPARATUS TO ANALYZE TIME SERIES DATA

(71) Applicant: Intel Corporation, Santa Clara, CA (US)

(72) Inventors: Darshan Iyer, Sunnyvale, CA (US); Nilesh K. Jain, Portland, OR (US)

(73) Assignee: Intel Corporation, Santa Clara, CA (US)

(*) Notice: Subject to any disclaimer, the term of this patent is extended or adjusted under 35 U.S.C. 154(b) by 835 days.

(21) Appl. No.: 15/673,069

(22) Filed: Aug. 9, 2017

(65) Prior Publication Data
US 2019/0050688 A1 Feb. 14, 2019

(51) Int. Cl.
| | | |
|---|---|---|
| G06K 9/62 | (2006.01) |
| G06K 9/00 | (2006.01) |
| A61B 5/0452 | (2006.01) |
| A61B 5/00 | (2006.01) |
| G06N 3/08 | (2006.01) |
| G06N 3/02 | (2006.01) |

(52) U.S. Cl.
CPC .............. *G06K 9/6267* (2013.01); *A61B 5/00* (2013.01); *A61B 5/0452* (2013.01); *A61B 5/7267* (2013.01); *A61B 5/7282* (2013.01); *G06K 9/00536* (2013.01); *G06K 9/6201* (2013.01); *G06K 9/6261* (2013.01); *G06K 9/6274* (2013.01); *G06N 3/08* (2013.01); *G06N 3/02* (2013.01)

(58) Field of Classification Search
USPC .......................................................... 706/20
See application file for complete search history.

(56) References Cited

U.S. PATENT DOCUMENTS

| | | | | |
|---|---|---|---|---|
| 9,118,639 | B2* | 8/2015 | Phegade | G06F 9/45558 |
| 9,342,376 | B2* | 5/2016 | Jain | G06F 9/5094 |
| 9,351,688 | B2* | 5/2016 | Iyer | A61B 5/0002 |
| 10,282,641 | B2* | 5/2019 | Jain | G06K 9/481 |
| 10,373,069 | B2* | 8/2019 | Kida | G06N 20/00 |
| 10,747,327 | B2* | 8/2020 | Iyer | G06K 9/6218 |
| 10,755,198 | B2* | 8/2020 | Iyer | G06K 9/628 |
| 2004/0147840 | A1* | 7/2004 | Duggirala | A61B 8/00 600/437 |
| 2008/0125668 | A1* | 5/2008 | Graupe | A61B 5/4362 600/511 |

* cited by examiner

*Primary Examiner* — Michael B Holmes
(74) *Attorney, Agent, or Firm* — Hanley, Flight & Zimmerman, LLC

(57) ABSTRACT

Methods, apparatus, systems and articles of manufacture to analyze time series data are disclosed. An example method includes sub sampling time series data collected by a sensor to generate one or more candidate samples of interest within the time series data. Feature vectors are generated for respective ones of the one or more candidate samples of interest. Classification of the feature vectors is attempted based on a model. In response to a classification of one of the feature vectors, the classification is stored in connection with the corresponding candidate sample.

21 Claims, 11 Drawing Sheets

METHODS AND APPARATUS TO ANALYZE TIME SERIES DATA

FIELD OF THE DISCLOSURE

This disclosure relates generally to machine learning, and, more particularly, to methods and apparatus to analyze time-series data.

BACKGROUND

It is important to find points of interest when analyzing time-series data. Such identification has wide applicability across many different fields. For example, time-series data such as an electrocardiogram (ECG or EKG) may be analyzed to identify data points in the ECG that correspond to pattern of data points expected to appear in a heartbeat signal.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Traditional machine learning approaches as applied to time-series data generally operate by finding a region of interest that includes a waveform having several time points, generating features from that region, building a model based on the features within the region, and then using that model against unknown subsequent data. Such an approach is well suited to time series data that includes an identifiable region of interest spanning multiple time points. However, some applications require identifying individual points localized in time having certain characteristics in the time-series data. Because traditional machine learning approaches require entire regions to be identified, some individual points may be missed (e.g., may not be identified). When individual points are missed, subsequent uses of the identified data points may be affected. For example, if a region representing a heartbeat is missed in an ECG, a patient's heart rate may be incorrectly identified. Moreover, entire regions must be formed for traditional identification, introducing delays in processing of data.

In examples disclosed herein, an adaptive framework is used to find localized points of interest in real time. Example approaches disclosed herein adapt to the changing characteristics of the underlying time-series. Example approaches disclosed herein filter portions of the analyzed data to reduce a processing requirement of the device processing the data. As a result, example approaches disclosed herein can be operated in real time and utilize low amounts of computing resources such that they can be used in resource-constrained platforms, such as wearable devices.

Figure 1:
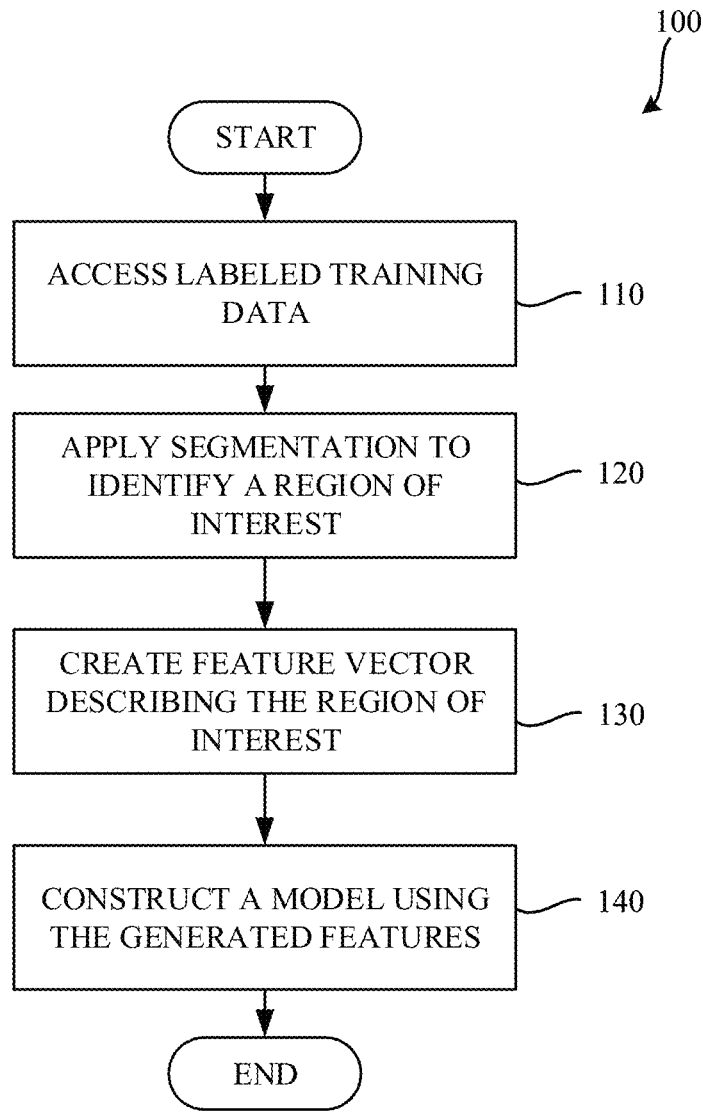
FIG. 1 is a flowchart illustrating an example prior-art approach to creating a model for identification of a feature in time-series data.

FIG. 1 is a flowchart illustrating a prior-art approach 100 to creating a model for identification of a feature in time-series data. In the prior art approach 100 of FIG. 1, labeled training data is accessed. (Block 110). Segmentation is applied to the labeled training data to identify a region of interest. (Block 120). The identified region is analyzed to create a feature vector describing the identified region of interest. (Block 130). A model is then created using the generated features and labels provided in the labeled training data. (Block 140). The model is then later used to identify and/or classify features within subsequently identified regions of interest.

Figure 2:
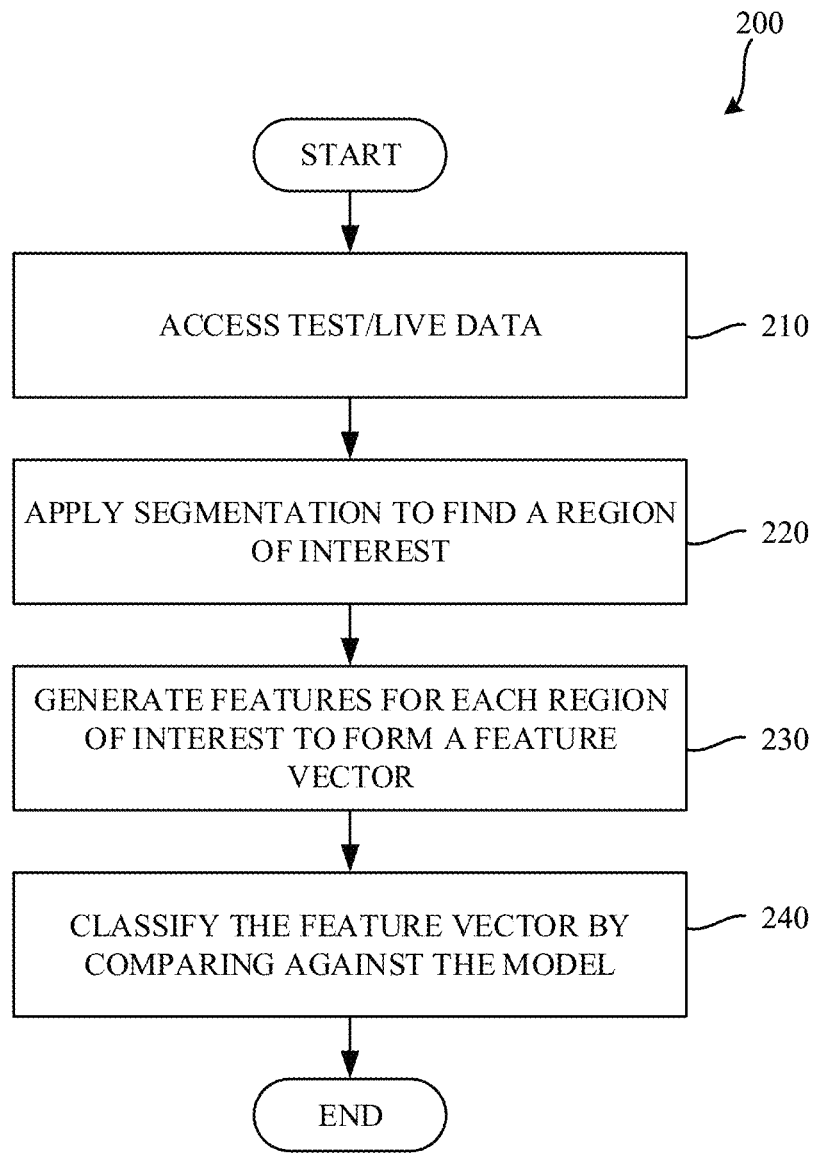
FIG. 2 is a flowchart illustrating an example prior-art approach to classifying time-series data using the model created using the example approach of FIG. 1.

FIG. 2 is a flowchart illustrating a prior-art approach 200 to classifying time-series data using the model created by the approach of FIG. 1. In the prior art approach 200 of FIG. 2, test and/or live data is accessed. (Block 210). Segmentation is applied to the accessed data to identify a region of interest within the data. (Block 220). The identified region is analyzed to create a feature vector describing the region. (Block 230). The model created in connection with the example approach of FIG. 1 is then used to classify and/or label the feature vector and/or underlying data point. (Block 240).

Figure 3:
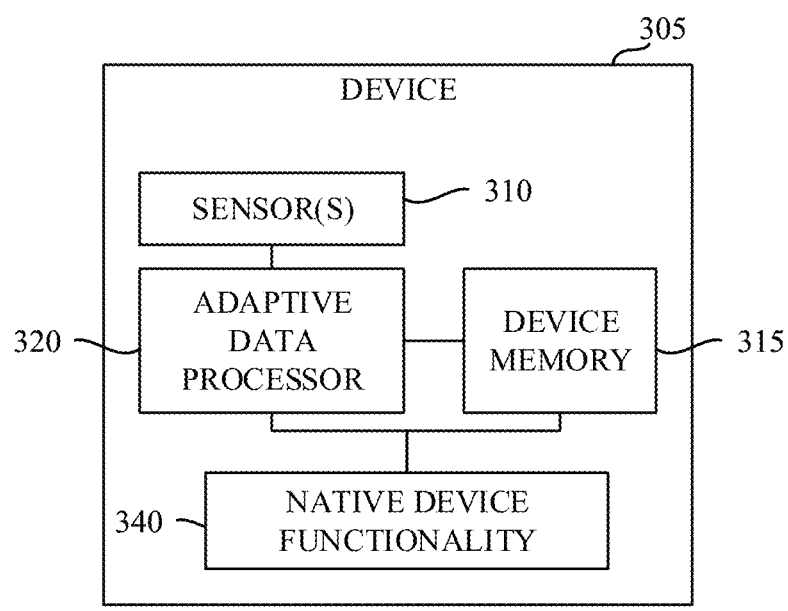
FIG. 3 is a block diagram of an example device constructed in accordance with the teachings of this disclosure to analyze time-series data.

FIG. 3 is a block diagram of an example device 305 constructed in accordance with the teachings of this disclosure. The example device 305 includes one or more sensors 310, a device memory 315, an adaptive data processor 320, and native device functionality 340. In the illustrated example of FIG. 3, the example device 305 is a wearable device. That is, the example device 305 is worn on and/or is carried by a user. However, any other past, present, and/or future type of device may additionally or alternatively be used. In some examples, the one or more sensors 310 capture biometric information from the user that can be processed by the example adaptive data processor 320 for use by the native device functionality 340. The native device functionality 340 can be any sort of functionality executed by the device 305 such as, for example, a fitness application (e.g., an "app").

The example one or more sensors 310 of the illustrated example of FIG. 3 collect data representing some property and/or characteristic encountered by the example device 305. For example, the example one or more sensors 310 may include an accelerometer that, when worn by a user, may be used to identify when the user takes a step. However, any other past, present, and/or future types and/or numbers of sensors may additionally or alternatively be used. In the illustrated example of FIG. 3, the example one or more sensors 310 are shown as sensors that are internal to the example device 305. However, in some examples, the example one or more sensors 310 may be implemented externally to the example device 305. For example, the example one or more sensors 310 may be connected to the example device 305 via wires and/or in a wireless fashion. In practice, any combination of wired, wireless, internal, and/or external sensors may additionally or alternatively be used.

The example device memory 315 of the illustrated example of FIG. 3 is implemented by any memory, storage device and/or storage disc for storing data such as, for example, flash memory, magnetic media, optical media, etc. Furthermore, the data stored in the example device memory 315 may be in any data format such as, for example, binary data, comma delimited data, tab delimited data, structured query language (SQL) structures, etc. While in the illustrated example the device memory 315 is illustrated as a single element, the example device memory 315 and/or any other data storage elements described herein may be implemented by any number and/or type(s) of memories. In the illustrated example of FIG. 3, the example device memory 315 stores labeled training data that can be used by the example adaptive data processor 320 to create a model to be used when analyzing data received from the example one or more sensors 310. In some examples, the example device memory 315 stores the model that is used by the example adaptive data processor 320. In some examples, the example adaptive data processor 320 stores identified and/or labeled data in the device memory 315.

The example adaptive data processor 320 of the illustrated example of FIG. 3 analyzes labeled training data to create a model that can be used to label and identify points in data received from the example one or more sensors 310. An example implementation of the example adaptive data processor 320 is described in further detail in connection with FIG. 4. The example adaptive data processor 320, having identified and/or labeled data points in the data received from the example one or more sensors 310, provides the identified and/or labeled data to the example device functionality 340 and/or to the example device memory 315.

The example device functionality 340 of the illustrated example of FIG. 3 utilizes the identified and/or labeled data to, for example, provide an output (e.g., a display) to a user of the device. For example, the example device 305 may be a heart rate monitoring device, in which case the device functionality 340 may output an identified heart rate of the user. However, the example device functionality 340 may utilize the labeled and/or identified data in any other manner to produce any type of output (e.g., visual, tactile, audible, etc.).

Figure 4:
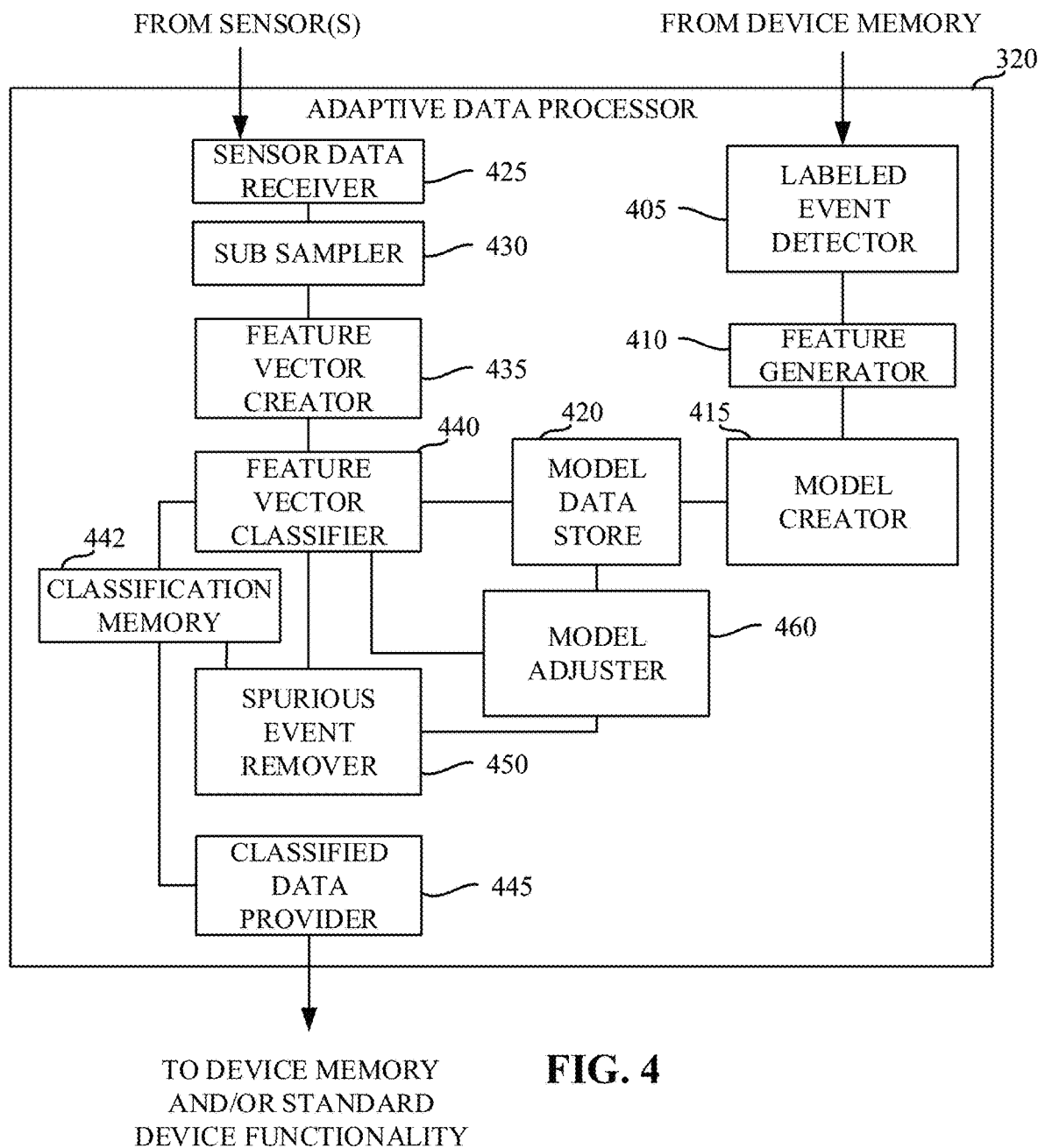
FIG. 4 is a block diagram of an example implementation of the example adaptive data processor of FIG. 3.

FIG. 4 is a block diagram of an example implementation of the example adaptive data processor of FIG. 3. The example adaptive data processor 320 of the illustrated example of FIG. 4 includes a labeled event detector 405, a feature generator 410, a model creator 415, a model data store 420, a sensor data receiver 425, a sub sampler 430, a feature vector creator 435, a feature vector classifier 440, a spurious event remover 450, a classified data provider 455, and a model adjuster 460.

In operation, the example labeled event detector 405 receives a labeled data set from the device memory 315 that provides labels for a sample data set (e.g., a heartbeat pattern with labels for a Q point, an R point, and an S point). The example feature generator 410 identifies features in association with labeled data points within the labeled data set. Using the identified features in the provided labels, the example model creator 415 creates and stores a model in the model data store 420.

In subsequent operation, the example sensor data receiver 425 receives data from one or more sensor(s) 310. Unlike the labeled data received by the labeled event detector 405, the sensor data received from the sensor(s) 310 is unlabeled. The example sub sampler 430 applies sub sampling to the received sensor data. The example feature creator 435 creates feature vectors based on the sub sampled data. Using the model stored in the example model data store 420, the example feature vector classifier 440 identifies and/or labels events within the sensor data based on the feature vectors created therefrom. The example labeled events can then be provided, by the classified data provider 445, to the device functionality 340 and/or to the example device memory 315 to facilitate operation of the device.

In some examples, the spurious event remover 450 identifies labeled events that are out of an expected order, and removes events from the labeled events to ensure that the labels conform to an expected order prior to those events being provided to the example standard device functionality 340 and/or the example device memory 315. In some examples, the model adjuster 460, updates the model stored in the example model data store 420.

The example labeled event detector 405 of the illustrated example of FIG. 4 accesses training data stored in the example device memory 315. In the example training data, one or more data points are identified by labels that classify the corresponding data point. In examples disclosed herein, the labels are applied to the training data by a developer and/or processing system. In examples disclosed herein, the example labeled training data includes a time series of data points, some of which may be labeled as indicative of exhibiting particular characteristics, properties, and/or features. In some examples, the data points are identified in connection with a time stamp to indicate the time at which the data point was collected, observed, etc. In some examples, the time series of data points are arranged chronologically. However, the time series data may be arranged in any other fashion. The example labeled event detector 405 reads the example training data to detect such labels.

The example feature generator 410 of the illustrated example of FIG. 4 generates features describing each of the data points identified by the example labeled event detector 405. In examples disclosed herein, features are created for all data points (e.g., including data points that do not have corresponding labels) and, in the aggregate, form a feature vector. However, in some examples, feature vectors are created only including features corresponding to labeled data points. Creating feature vectors including all data points as part of the training and/or model creation process ensures that data points which are not classified in the training data are accounted for in the model.

The example model creator 415 of the illustrated example of FIG. 4 creates a model based on the labels and the corresponding feature vectors. In examples disclosed herein, unlabeled data points are considered for purposes of creation of the model. In examples disclosed herein, the example model is implemented using an artificial neural network (ANN). However, any other type of model and/or modeling approach may additionally or alternatively be used.

The example model data store 420 of the illustrated example of FIG. 4 stores the example model created by the example model creator 415. In examples disclosed herein, the example model data store 420 is implemented by any memory, storage device and/or storage disc for storing data such as, for example, flash memory, magnetic media, optical media, etc. Furthermore, the data stored in the example model data store 420 may be in any data format such as, for example, binary data, comma delimited data, tab delimited data, structured query language (SQL) structures, etc. While in the illustrated example the example model data store 420 is illustrated as a single element, the example model data store 420 and/or any other data storage elements described herein may be implemented by any number and/or type(s) of memories. In some examples, the example model data store 420 is implemented as a component of the example device memory 315.

The example sensor data receiver 425 of the illustrated example of FIG. 4 receives sensor data from the one or more sensors 310. In examples disclosed herein, the sensor data is analog data, and the example sensor data receiver 425 implements an analog to digital converter. However, any other approach to accessing sensor data may additionally or alternatively be used. For example, the sensor data receiver 425 may access the data wirelessly (e.g., e.g., via a Bluetooth interface).

The example sub sampler 430 of the illustrated example of FIG. 4 processes the sensor data received by the example sensor data receiver 425 to select data points as candidate samples. The example sub sampler 430 selects such candidate samples by deriving one or more mathematical properties corresponding to each data point and selecting the samples based on the derived mathematical properties. In examples disclosed herein, the sub sampler 430 identifies a first order derivative, and selects zero crossings in the first order derivative. However, any other mathematical property such as, for example, a second order derivative, an integral, a moving average, etc. may additionally or alternatively be used. Such an approach ensures that the sub sampler 430 selects appropriate data points in the data set (e.g., peaks, valleys, inflection points, etc.) as the candidate samples. Such selected candidate samples go on to be processed by the example feature vector creator 435 and/or the example feature vector classifier 440. In examples disclosed herein, the number of selected candidate samples is less than the total number of data points collected by the example sensor data receiver 425. That is, instead of generating a feature vector for every sample data point and attempting to classify those feature vectors, sub sampling reduces the number of feature vectors and/or attempted classifications. Moreover, because the number of feature vectors is reduced, such classification processing can be performed using fewer computing resources as compared to approaches that do not utilize sub sampling. As a result, devices with less computing power such as wearable devices may be able to more efficiently process larger volumes of incoming sensor data.

The example feature vector creator 435 of the illustrated example of FIG. 4 creates a feature vector for each of the selected candidate samples. Because there are fewer candidate samples than all received samples, the amount of data points for which a feature vector is created is reduced as compared to preparing feature vectors for all data points received from the sensors.

The example feature vector classifier 440 of the illustrated example of FIG. 4 attempts to classify a feature vector using the model stored in the example model data store 420. In examples disclosed herein, the example feature vector classifier 440 identifies one or more labels corresponding to one or more labels supplied during the creation of the model (e.g., a label detected by the labeled event detector 405). In some examples, classification of an example feature vector is attempted, but no label (e.g., no classification) is identified. In examples disclosed herein, the example feature vector classifier 440 stores the identified labels and/or classifications in the classification memory 442. In some examples, to conserve computing resources (e.g., storage space), only those feature vectors that result in labels and/or classifications are stored in the example classification memory 442.

The example classification memory 442 of the illustrated example of FIG. 4 stores the classification(s) identified by the example feature vector classifier 440 in connection with the classified data points accessed by the sensor data receiver 425. In examples disclosed herein, the example classification memory 442 is implemented by any memory, storage device and/or storage disc for storing data such as, for example, flash memory, magnetic media, optical media, etc. Furthermore, the data stored in the example classification memory 442 may be in any data format such as, for example, binary data, comma delimited data, tab delimited data, structured query language (SQL) structures, etc. While in the illustrated example the example classification memory 442 is illustrated as a single element, the example classification memory 442 and/or any other data storage elements described herein may be implemented by any number and/or type(s) of memories. In some examples, the example classification memory 442 is implemented as a component of the example device memory 315.

The example classified data provider 445 of the illustrated example of FIG. 4 provides the labels and corresponding data points to the example device memory 315 and/or the example device functionality 340. In some examples, the example classified data provider 445 provides classified data after it has been reviewed and/or altered by the spurious event remover 450.

The example spurious event remover 450 of the illustrated example of FIG. 4 exploits an expected time relationship between the classified data points stored in the classification memory 442 to remove spurious classifications. For example, if the data represented by the incoming sensor data was related to a user's heartbeat, the identified and relabeled data points would expected to be in an order of a Q point, followed by an R point, followed by an S point. If the label data points were not in the expected order (e.g., were in an order of QSRS, instead of QRS), one or more of the data points (e.g., the data point corresponding to the first S label) are removed to ensure the proper order (e.g., QRS).

The example model adjuster 460 of the illustrated example of FIG. 4 accesses labeled validation data to validate the model stored in the example model data store 420. In examples disclosed herein, the example model adjuster 460 causes the example feature vector creator 435 to generate a feature vector for each of the labeled samples in the labeled validation data. The example model adjuster 460 causes the example feature vector classifier 440 to classify the created feature vector(s). The example model adjuster 460 compares the classification of the feature vector derived by the example feature vector classifier 440 to the label provided with the labeled validation data to determine whether the classification was correct. If the example model adjuster 460 determines that the classification was not correct, the example model adjuster 460 adjusts the model parameters and updates the model to account for the misclassified sample. That is, feedback is provided to enable the model to be dynamically updated and/or adjusted based on data received from the one or more sensor(s) 310. In examples disclosed herein, the properties of the model such as an area of influence are adjusted to account for the misclassifications. However, any other model properties may additionally or alternatively be adjusted and/or modified.

While an example manner of implementing the example adaptive data processor 320 of FIG. 3 is illustrated in FIG. 4, one or more of the elements, processes and/or devices illustrated in FIG. 4 may be combined, divided, re-arranged, omitted, eliminated and/or implemented in any other way. Further, the example labeled event detector 405, the example feature generator 410, the example model creator 415, the example model data store for 20, the example sensor data receiver 425, the example sub sampler 430, the example feature vector creator 435, the example feature vector classifier 440, the example classification memory 442, the example spurious event remover 450, the example classified data provider 445, the example model adjuster 460, and/or, more generally, the example adaptive data processor 320 of FIGS. 3 and/or 4 may be implemented by hardware, software, firmware and/or any combination of hardware, software and/or firmware. Thus, for example, any of the example labeled event detector 405, the example feature generator 410, the example model creator 415, the example model data store for 20, the example sensor data receiver 425, the example sub sampler 430, the example feature vector creator 435, the example feature vector classifier 440, the example classification memory 442, the example spurious event remover 450, the example classified data provider 445, the example model adjuster 460, and/or, more generally, the example adaptive data processor 320 of FIGS. 3 and/or 4 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example labeled event detector 405, the example feature generator 410, the example model creator 415, the example model data store 420, the example sensor data receiver 425, the example sub sampler 430, the example feature vector creator 435, the example feature vector classifier 440, the example classification memory 442, the example spurious event remover 450, the example classified data provider 445, the example model adjuster 460, and/or, more generally, the example adaptive data processor 320 of FIGS. 3 and/or 4 is/are hereby expressly defined to include a non-transitory computer readable storage device or storage disk such as a memory, a digital versatile disk (DVD), a compact disk (CD), a Blu-ray disk, etc. including the software and/or firmware. Further still, the example adaptive data processor 320 of FIGS. 3 and/or 4 may include one or more elements, processes and/or devices in addition to, or instead of, those illustrated in FIG. 4, and/or may include more than one of any or all of the illustrated elements, processes and devices.

Figure 5:
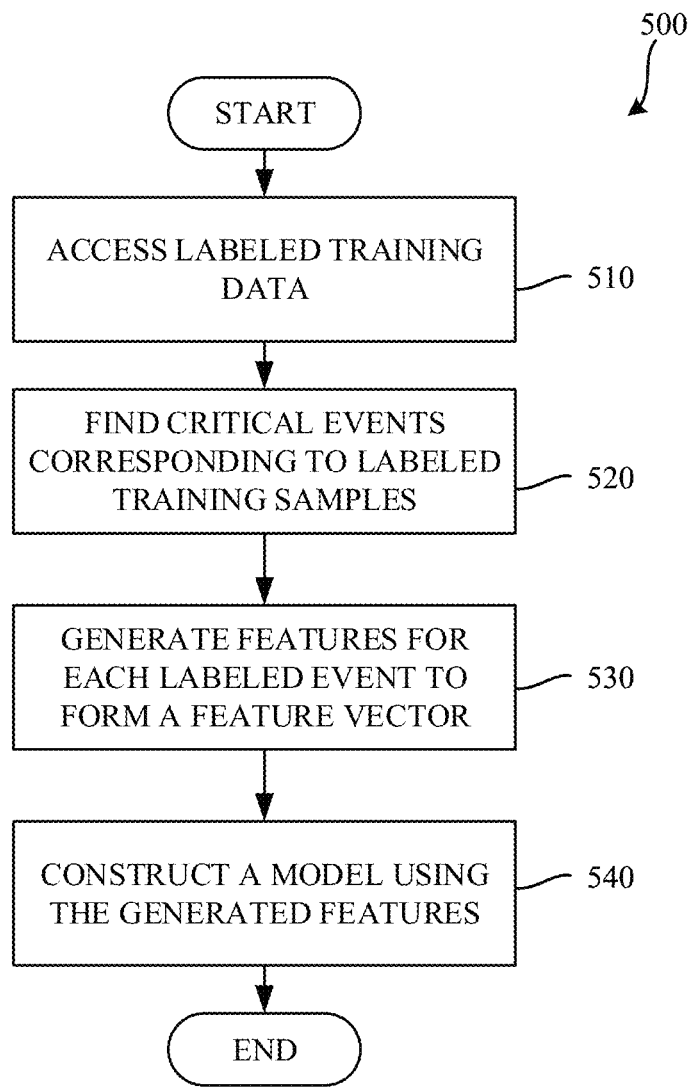
FIG. 5 represents example machine-readable instructions which, when executed, cause the example adaptive data processor of FIGS. 3 and/or 4 to construct a model for analyzing time-series data.
Figure 7:
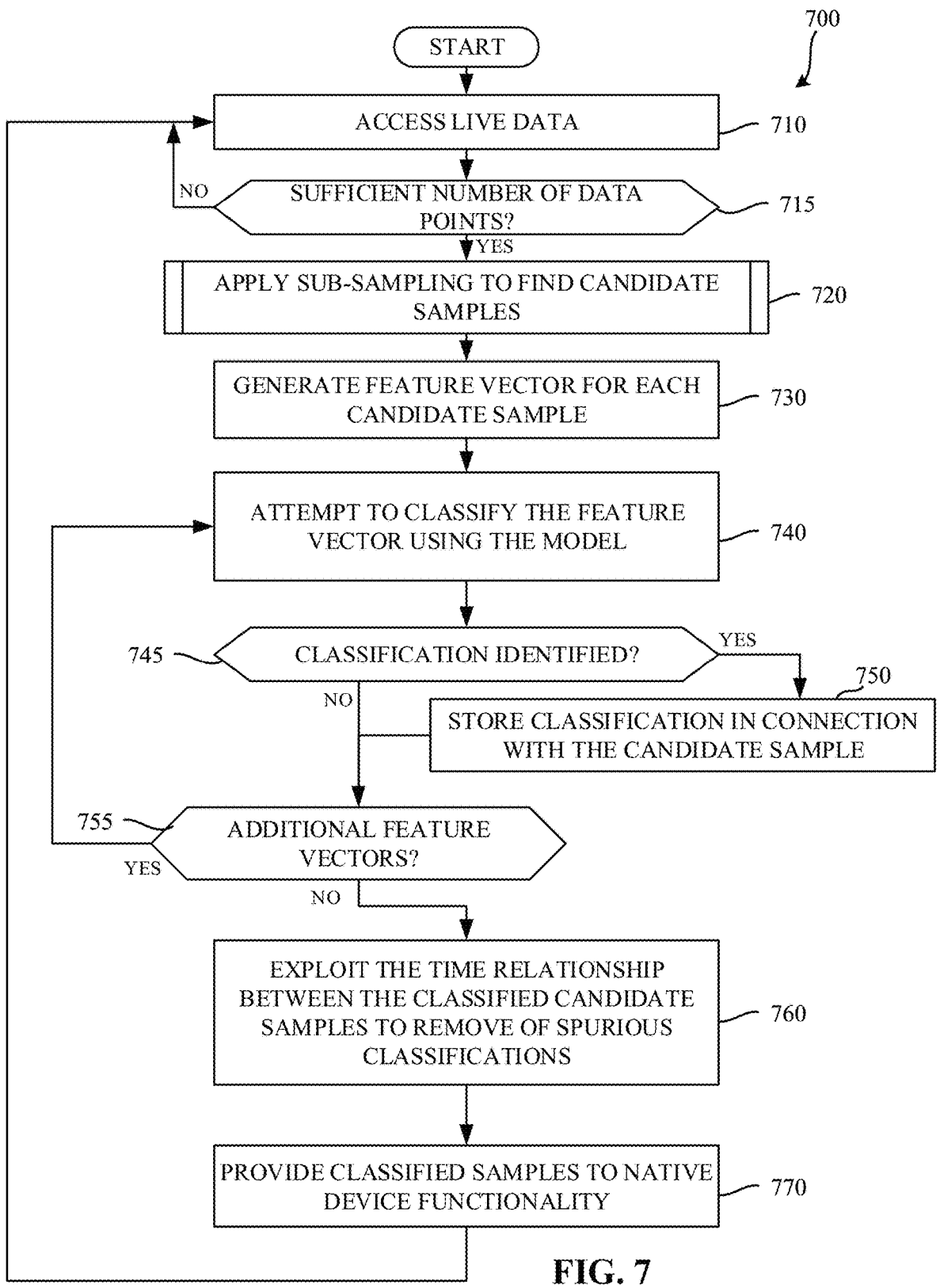
FIG. 7 represents example machine-readable instructions which, when executed, cause the example adaptive data processor of FIGS. 3 and/or 4 to analyze time-series data using the model.
Figure 8:
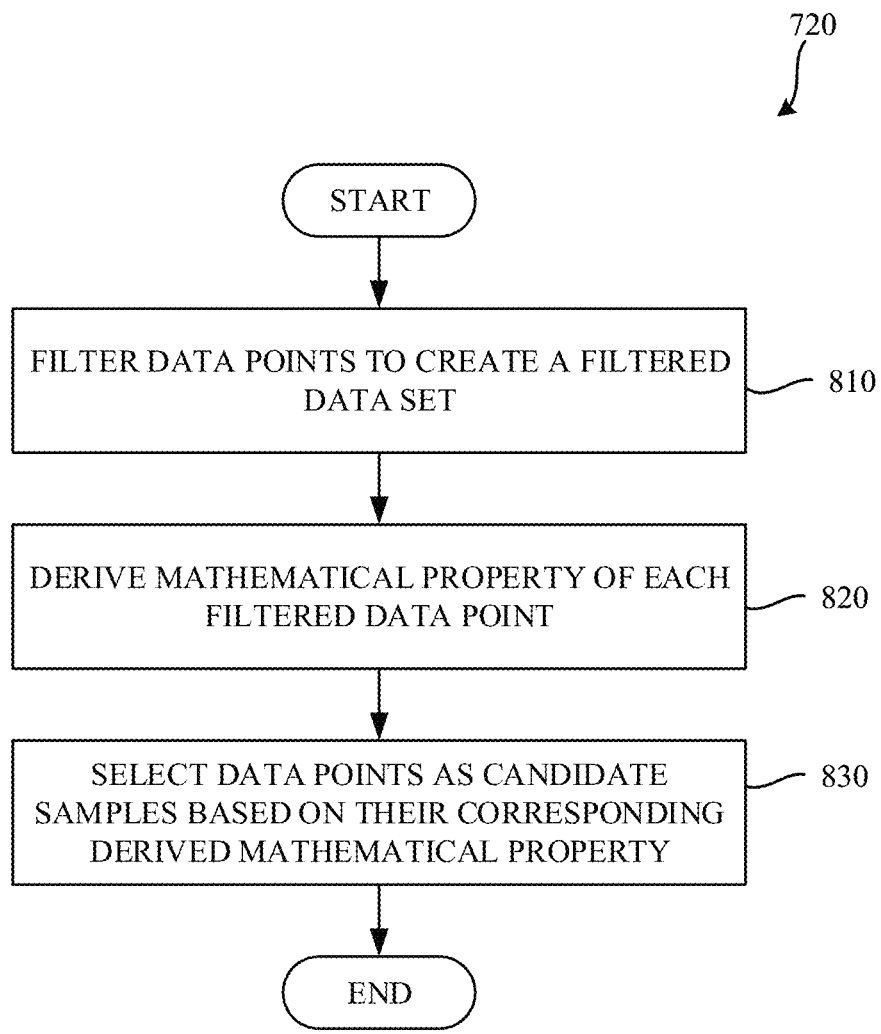
FIG. 8 represents example machine-readable instructions which, when executed, cause the example adaptive data processor of FIGS. 3 and/or 4 to utilize sub sampling to identify candidate samples.

Flowcharts representative of example machine readable instructions for implementing the example adaptive data processor 320 of FIGS. 3 and/or 4 are shown in FIGS. 5, 7, 8, and/or 10. In these examples, the machine readable instructions comprise a program for execution by a processor such as the processor 1112 shown in the example processor platform 1100 discussed below in connection with FIG. 11. The program may be embodied in software stored on a non-transitory computer readable storage medium such as a CD-ROM, a floppy disk, a hard drive, a digital versatile disk (DVD), a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowcharts illustrated in FIGS. 5, 7, 8, and/or 10, many other methods of implementing the example adaptive data processor 320 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIGS. 5, 7, 8, and/or 10 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

FIG. 5 represents example machine-readable instructions which, when executed, cause the example adaptive data processor 320 of FIGS. 3 and/or 4 to construct a model for analyzing time-series data. The example process 500 of the illustrated example of FIG. 5 begins when the example labeled event detector 405 accesses labeled training data from the device memory 315. (Block 510). In examples disclosed herein, the example labeled training data includes a time series of data points, some of which may be labeled as indicative of exhibiting particular characteristics, properties, and/or features. In some examples, the data points are identified in connection with a time stamp to indicate the time at which the data point was collected, observed, etc. In some examples, the time series of data points are arranged chronologically. However, the time series data may be arranged in any other fashion.

In examples disclosed herein, the time series of data points may represent a heartbeat waveform, with labels provided at a Q point, an R point, and an S point of the heartbeat waveform (e.g., indicating a QRS complex). Of course, any other type of labeled data may additionally or alternatively be used. For example, the labeled data may correspond to accelerometer data used to detect once a user has taken a step (e.g., in a step counting and/or fitness application). In examples disclosed herein, the labeled data is pre-populated in the device memory 315 to enable the device to generate the model. An example labeled waveform (e.g., time series data) is shown in the illustrated example of FIG. 6.

Figure 6:
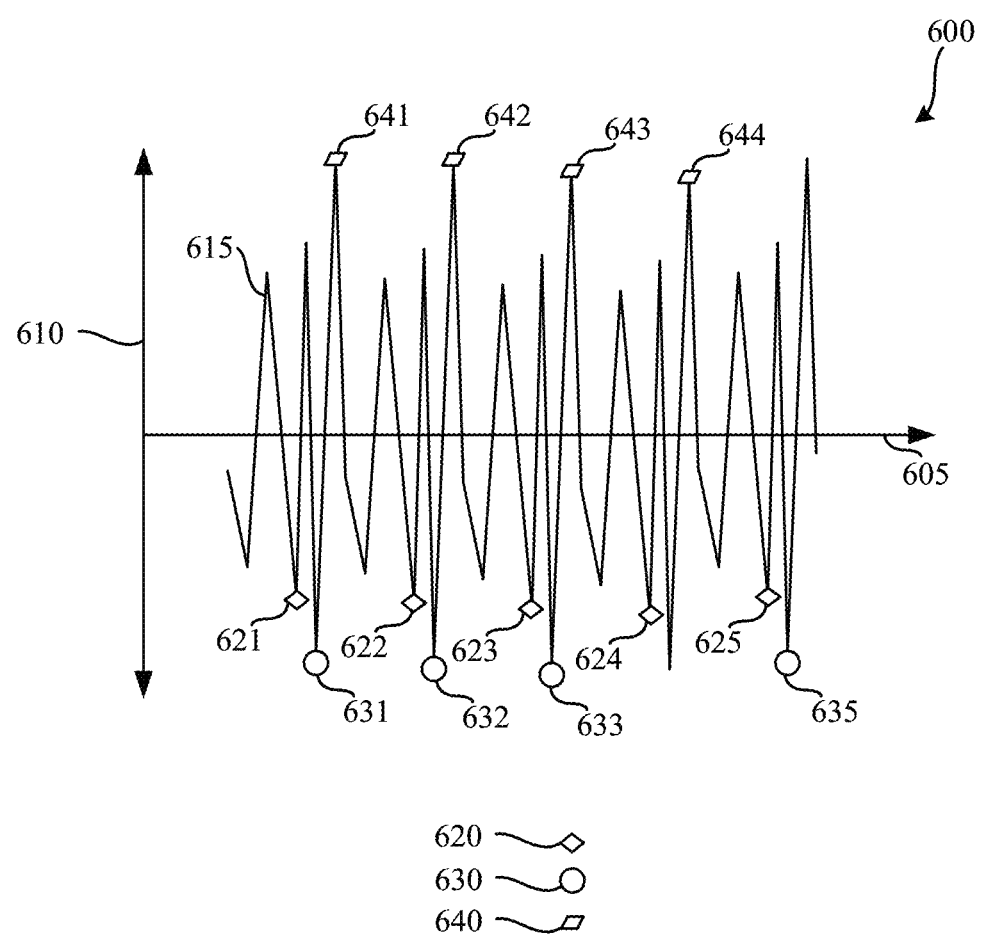
FIG. 6 is a diagram of example labeled time-series data that may be used by the example adaptive data processor of FIGS. 3 and/or 4 to construct the model for analyzing time-series data.

FIG. 6 is a diagram of example labeled time-series data that may be used by the example adaptive data processor 320 of FIGS. 3 and/or 4 to construct a model for analyzing time-series data. The example diagram 600 the illustrated example of FIG. 6 includes a horizontal axis 605, representing time. The example diagram 600 the illustrated example of FIG. 6 includes a vertical axis 610 representing a value of a corresponding data point. In the example diagram 600 of the illustrated example of FIG. 6, a waveform 615 represents labeled data over time. In the illustrated example of FIG. 6, three different types of labels 620, 630, 640 are used to show different points in the training data waveform. The first label 620 is applied to a first peak 621, a second peak 622, a third peak 623, a fourth peak 624, and a fifth peak 625 within the waveform 615. The second label 630 is applied to a sixth peak 631, a seventh peak 632, an eighth peak 633, and a ninth peak 635. In the illustrated example of FIG. 6, a peak intermediate the eighth peak 633 and the ninth peak 635 that would otherwise be expected to be labeled using the second label 630 does not have a corresponding label. The third label 640 is applied to a tenth peak 641, an eleventh peak 642, a twelfth peak 643, and a thirteenth peak 644. In the example labeled training data, data points that are not labeled are considered null labels. In some examples, the null labeled data points are factored in to the creation of the model.

In the illustrated example of FIG. 6, the waveform 615 is substantially periodic. For example, a patient's heart is expected to beat repeatedly, and produce a substantially similar pattern in each beat. However, minor differences in each of the repeated beats can occur. For example, amplitudes of particular peaks, time delays between labeled data points, etc. may vary from beat to beat. In some examples, the waveform is a-periodic and, as a result, the waveform might not be expected to be repeated in a periodic fashion. For example, an accelerometer used to detect when a user has taken a step might produce an a-periodic waveform while the user is moving or stepping in a non-periodic fashion (e.g., is standing at a desk).

Returning to FIG. 5, upon accessing the labeled training data (block 510), the example labeled event detector 405 identifies critical events corresponding to labeled samples in the training data. (Block 520). In some examples, the critical events correspond to labeled data points. In some examples, unlabeled data points are considered as well, as inclusion of such data points in consideration of the construction of the model may result in a more reliable and/or error-resistant model.

Using the identified events, the example feature generator 410 generates features for each of the labeled events to form a feature vector. (Block 530). The example feature vectors describe properties of the identified events and, in some examples, properties of data points proximate in time to the corresponding critical events. Using the example feature vectors created by the example feature generator 410, the example model creator 415 constructs a model using the generated features. (Block 540). In examples disclosed herein, the model is stored in the example model data store 420. The example model may then be used to subsequently identify and/or classify data points and live data as corresponding to one of the types of labels.

While in the illustrated example of FIG. 5, training data is read from a device memory and a model is created within the device based thereon, in some examples, the model itself may be pre-populated in the device memory 315. Pre-populating the model in the device memory 315 reduces the amount of processing time that would be required of the adaptive data processor 320 (e.g., processing time associated with the construction and/or generation of the model). In such an example, the model may be generated by an external device (e.g., a server) and pre-populated on many devices.

FIG. 7 represents example machine-readable instructions which, when executed, cause the example adaptive data processor of FIGS. 3 and/or 4 to analyze time-series data using the model. The example process 700 of the illustrated example of FIG. 7 begins when the example sensor data receiver 425 accesses live data from one or more sensors 310. (Block 710). In examples disclosed herein, the example sensor data receiver 425 aggregates data samples from the sensors in a memory (e.g., a cache). In examples disclosed herein, the example sensor data receiver 425 periodically accesses data from the sensors. In examples disclosed herein, sensor data is accessed once every millisecond. However, any other frequency may additionally or alternatively be used.

The example sub sampler 430 determines whether a sufficient number of data points have been collected by the example sensor data receiver 425. (Block 715). In examples disclosed herein, the example sub sampler 430 identifies that a sufficient number of data points have been collected when there are more than a threshold number of data points (e.g., one hundred data points, one thousand data points, ten thousand data points, etc.) In some examples, the threshold number of data points may be one data point. If the example sub sampler 430 identifies that the threshold number of data points has not been collected (e.g., block 715 returns result of NO), the example sensor data receiver 425 continues to access live data (block 710) until the sufficient number of data points has been collected (e.g., until block 715 returns a result of YES).

Upon identifying that a sufficient number of data points have been collected (block 715 returns a result of YES), the example sub sampler 430 applies sub sampling to the accessed live data find candidate samples. (Block 720). In examples disclosed herein, the example sub sampler 430 determines properties in connection with each of the data points collected by the example sensor data receiver 425, and selects one or more samples as candidate samples based on one or more of the properties. An example approach to sub sampling is described below in connection with FIG. 8. As a result of the sub sampling process, candidate samples are identified.

In a streaming data scenario (e.g., where each data point is received sequentially), while the sub sampler may operate on a number of previously received samples to determine a property in connection with the most recently received data point, the example sub sampler 430 may, in some examples, only evaluate whether the most recently received data point should be considered a candidate sample.

The example feature vector creator 435, based on the candidate samples selected by the sub sampler 430, generates a feature vector for each candidate sample. (Block 730). In examples disclosed herein, the number of candidate samples is lower than the total number of data points. That is, instead of generating a feature vector for every sample data point and attempting to classify each of those feature vectors, sub sampling reduces the number of feature vectors and/or attempted classifications. More particularly, feature vectors are not generated for every sampled data point, but instead are generated only for those sampled data points identified as candidate samples. As a result, such processing can be performed using fewer computing resources as compared to approaches that do not utilize sub sampling. Moreover, devices with less computing power such as wearable devices may be able to more efficiently process larger volumes of incoming sensor data.

The example feature vector classifier 440 attempts to classify the feature vector(s) created by the example feature vector creator 435 using the model stored in the example model data store 420. (Block 740). The example feature vector classifier 440 determines whether a classification has been identified for the feature vector. (Block 745). If a classification has been identified for the example feature vector (e.g., block 745 returns a result of YES), the example feature vector classifier 440 stores the classification in connection with the candidate sample associated with the feature vector being analyzed in the example classification memory 442. (Block 750). Upon either storing the classification (block 750), or the feature vector classifier 440 not identifying a classification (e.g., block 745 returning a result of NO), the example feature vector classifier 440 determines whether any additional feature vectors exist for classification. (Block 755). If additional feature vectors exist for classification (e.g., block 755 returns result of YES), the example process of blocks 740 through 755 is repeated until no additional feature vectors exist.

Upon the feature vector determining that it has attempted to classify all available feature vectors (e.g., block 755 returns a result of NO), the example spurious event remover exploits the time relationship between the classified candidate samples to remove spurious classifications. For example, if the data represented by the incoming sensor data was related to a user's heartbeat, the identified and relabeled data points would expected to be in an order of a Q point followed by an R point, followed by an S point. If the labeled data points were not in the expected order, one or more of the data points are removed to ensure the proper order. Upon removal of the spurious events, the example classified data provider 445 provides the classified samples to the standard device functionality 340 and/or saves the classified samples in the device memory 315. (Block 770). The example process of FIG. 7 then repeats.

FIG. 8 represents example machine-readable instructions which, when executed, cause the example adaptive data processor of FIGS. 3 and/or 4 to utilize sub sampling to identify candidate samples. The example process 720 of the illustrated example of FIG. 8 begins when the example sub sampler 430 filters data points to create a filtered data set. (Block 810). In examples disclosed herein, the filtering applied is a low-pass filter to remove high-frequency noise present in the data sensor data. However, any other type of filtering may additionally or alternatively be applied.

The example sub sampler 430 identifies one or more mathematical properties of each filtered data point (which may be absolute (e.g., a property of only that data point) or relative (e.g., a property of the data point as compared to one or more adjacent and/or near data points)) to create a derived data set. (Block 820). In examples disclosed herein, the mathematical property is a first derivative (e.g., a rate of change from the prior data point). However, any other type of mathematical property may additionally or alternatively be derived such as, for example, an integral, a second derivative, a third derivative, a fourth derivative, an $n^{th}$ derivative, a moving average, etc. In some examples, multiple mathematical properties are determined.

The example sub sampler 430 selects data points as candidate samples based on their corresponding mathematical properties. (Block 830). In examples disclosed herein, data points are selected when their corresponding first derivative is zero (e.g., zero crossings are identified), indicating a peak and/or a valley in the filtered data set. However, any other approach to selecting data points based on their derived mathematical property may additionally or alternatively be used. For example, a zero crossing of a second derivative may be used to identify an inflection point in the filtered data set. In some examples, one or more criteria may be used to select data points as candidate data points such as, for example, a zero crossing of the first derivative (e.g., a peak or a valley of the filtered data set), and a zero crossing of the second derivative (e.g., an inflection point in the filtered data set). Of course, any number and/or combination of criteria may be used to identify candidate samples. Upon the selection of data points as the candidate samples, control proceeds to block 730 of FIG. 7 where feature vectors are generated for each selected candidate sample.

Figure 9:
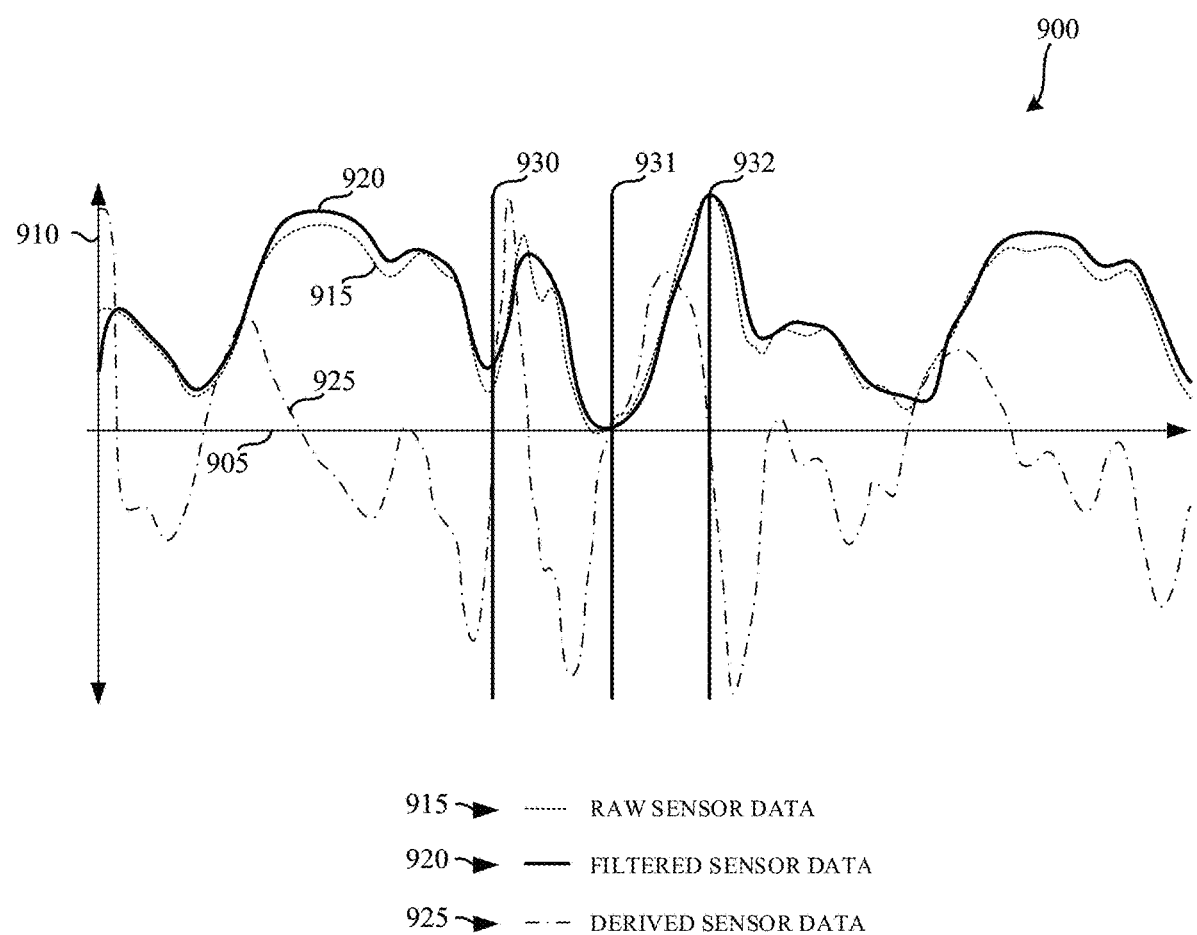
FIG. 9 is a diagram of example sub sampled data generated in connection with the example process of FIG. 7.

FIG. 9 is an example graph of data points and sub sampled data determined in connection with each of those data points. Example graph 900 of the illustrated example of FIG. 9 includes a horizontal axis 905 representing time, and a vertical axis 910 representing amplitude. In the example graph 900 of the illustrated example of FIG. 9, example collected data 915 (e.g., raw and/or unmodified sensor data), example filtered data 920, and example derived data 925 is shown. In the illustrated example of FIG. 9, candidate samples 930, 931, and 932 are identified when there are zero crossings of the derived data. Of course, any other approach for selecting data points as candidates may additionally or alternatively be used. While in the illustrated example of FIG. 9, three data points are selected as candidate samples, any other number of candidate samples may additionally or alternatively be selected.

Figure 10:
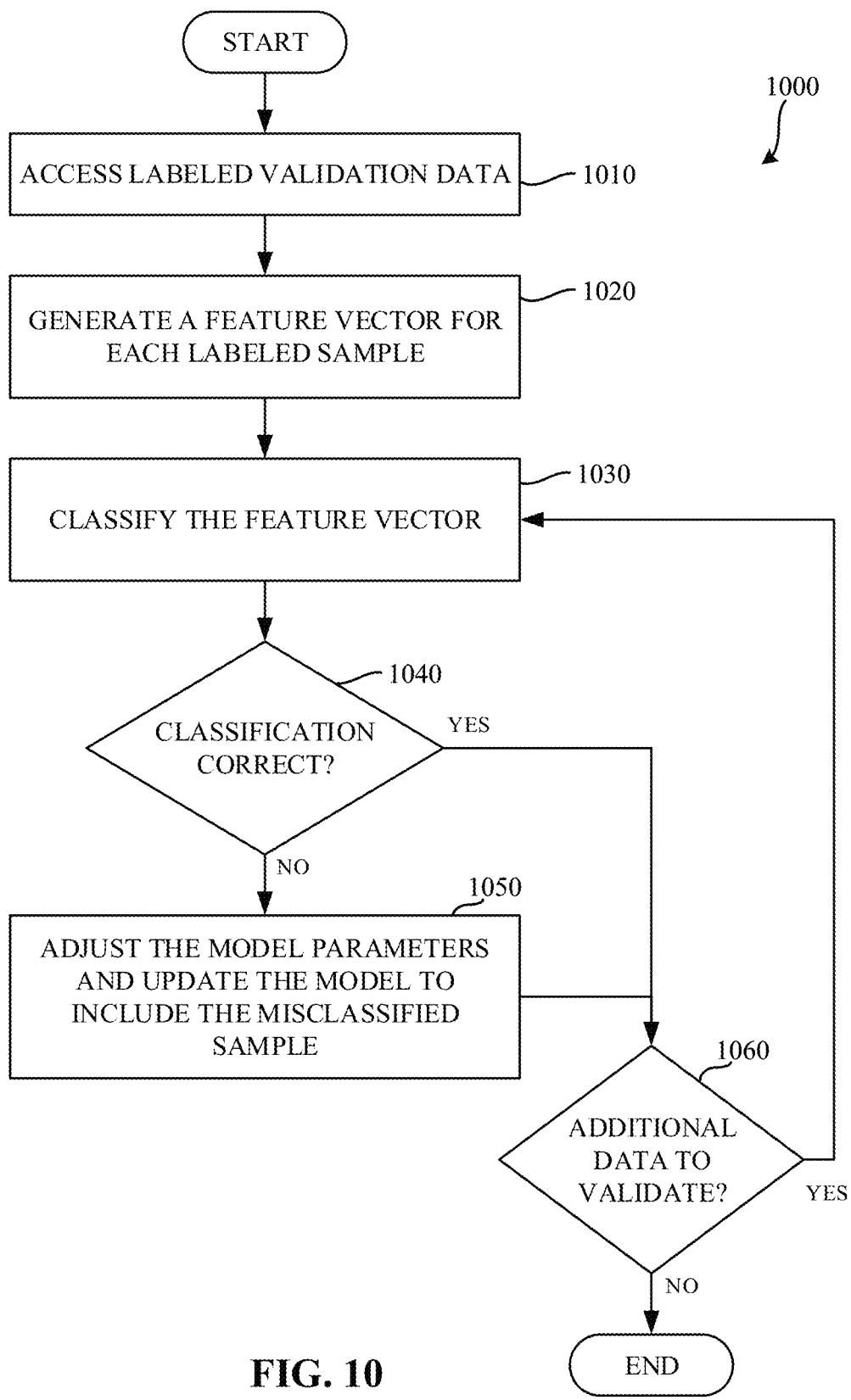
FIG. 10 represents example machine-readable instructions which, when executed, cause the example adaptive data processor of FIGS. 3 and/or 4 to validate and/or adapt the example model.

FIG. 10 represents example machine-readable instructions which, when executed, cause the example adaptive data processor of FIGS. 3 and/or 4 to validate and/or adapt the example model. The example process 1000 of the illustrated example of FIG. 10 begins when the example model adjuster 460 accesses labeled validation data. (Block 1010). In examples disclosed herein, the labeled validation data includes data provided by the spurious event remover 450 and/or may label data points that were identified by the spurious event remover 450 as incorrect as null labels in the labeled validation data. However, the labeled validation data may be accessed in any other fashion. For example, the example labeled validation data may be stored in the device memory and/or be provided by an external validation data source. The example model adjuster 460 causes the example feature vector creator 435 to generate a feature vector for each of the labeled samples in the labeled validation data. (Block 1020). The example model adjuster 460 causes the example feature vector classifier 440 to classify the feature vector. (Block 1030). The example model adjuster 460 compares the classification of the feature vector derived by the example feature vector classifier 440 (in block 1030) to the label provided with the labeled validation data (in block 1010) to determine whether the classification was correct. (Block 1040). If the example model adjuster 460 determines that the classification was not correct (e.g., block 1040 returns result of NO), the example model adjuster 460 adjusts the model parameters and updates the model to include the misclassified sample. (Block 1050). In examples disclosed herein, the properties of the model such as an area of influence, weighting values, etc. are adjusted to account for the misclassifications.

If the classification was correct (e.g., block 1040 returning a result of YES) and/or after adjusting the model parameters (e.g., block 1050), the example model validator 460 determines whether there is any additional data to validate. (Block 1060). If there is additional data to validate (e.g., block 1060 returns a result of YES), control proceeds to block 1030 where the example model adjuster 460 instructs the example feature vector classifier 440 to classify the subsequent feature vector. The example process of blocks 1030, 1040, 1050, and 1060 repeats until the example model adjuster 460 determines that there is no additional data to validate (e.g., until block 1060 returns a result of NO).

In examples disclosed herein, the example process 1000 of the illustrated example of FIG. 10 is repeated periodically. However, the example process 1000 of the illustrated example of FIG. 10 may be repeated a periodically (e.g., on demand).

Figure 11:
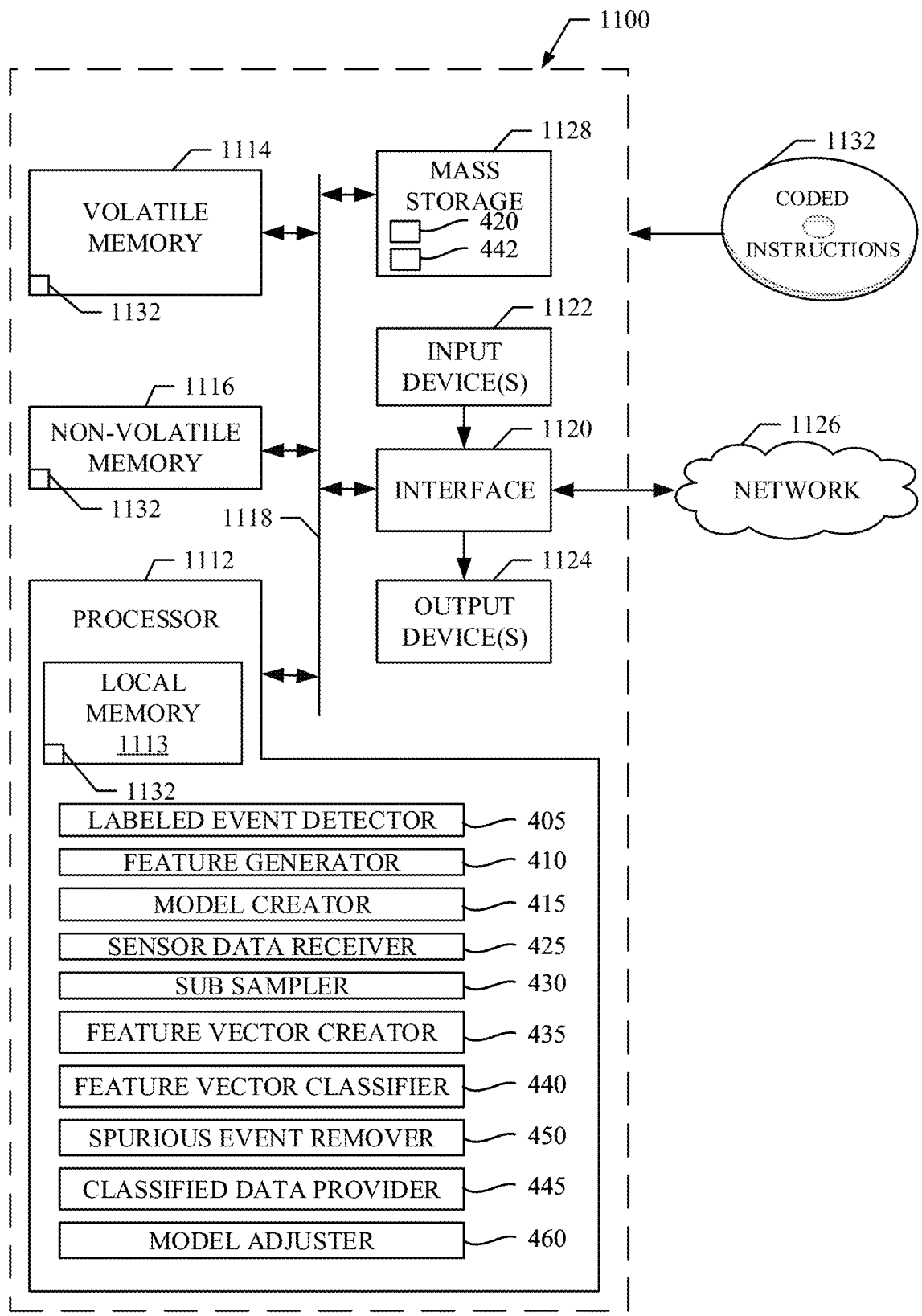
FIG. 11 is a block diagram of an example processor platform capable of executing the instructions of FIGS. 5, 7, 8, and/or 10 to implement the example adaptive data processor of FIGS. 3 and/or 4.

FIG. 11 is a block diagram of an example processor platform 1100 capable of executing the instructions of FIGS. 5, 7, 8, and/or 10 to implement the example adaptive data processor 320 of FIGS. 3 and/or 4. The processor platform 1100 can be, for example, a server, a personal computer, a mobile device (e.g., a cell phone, a smart phone, a tablet such as an iPad), a personal digital assistant (PDA), an Internet appliance, a DVD player, a CD player, a digital video recorder, a Blu-ray player, a gaming console, a personal video recorder, a set top box, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors or controllers from any desired family or manufacturer. The hardware processor may be a semiconductor based (e.g., silicon based) device. In this example, the processor 1112 implements the example labeled event detector 405, the example feature generator 410, the example model creator 415, the example sensor data receiver 425, the example sub sampler 430, the example feature vector creator 435, the example feature vector classifier 440, the example spurious event remover 450, the example classified data provider 445, and/or the example model adjuster 460.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 may be implemented by flash memory and/or any other desired type of memory device. Access to the main memory 1114, 1116 is controlled by a memory controller.

The processor platform 1100 of the illustrated example also includes an interface circuit 1120. The interface circuit 1120 may be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, an accelerometer, a heart rate sensor, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1120 of the illustrated example, thus, typically includes a graphics driver card, a graphics driver chip and/or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

The coded instructions 1132 of FIGS. 5, 7, 8, and/or 10 may be stored in the mass storage device 1128, in the volatile memory 1114, in the non-volatile memory 1116, and/or on a removable tangible computer readable storage medium such as a CD or DVD.

From the foregoing, it will be appreciated that example methods, apparatus and articles of manufacture have been disclosed that enable efficient processing of data to identify time-localized data samples of interest. In examples disclosed herein, because sub sampling is used to identify candidate samples prior to attempting to classify those candidate samples, an amount of computing resources utilized by attempting to classify samples that do not result in labels being identified is reduced. As a result of the reduction in computing resources, approaches disclosed herein enable such processing to be performed on resource-constrained devices such as, for example, smart-watches, wearable devices, etc.

Example 1 includes an apparatus for analyzing time-series data, the apparatus comprising a sub sampler to sub sample time series data to identify one or more candidate samples of interest within the time series data, a feature vector creator to create feature vectors corresponding to respective ones of the one or more candidate samples of interest, and a feature vector classifier to attempt to classify the feature vectors based on a model, the feature vector classifier to, in response to a classification of one of the feature vectors, store the classification in connection with the corresponding candidate sample in a memory.

Example 2 includes the apparatus of example 1, further including a spurious event remover to identifying that an order of classifications of the one or more candidate samples is not in an expected order, the spurious event remover to, in response to the identifying that the order of classifications is not in the expected order, remove one or more of the classifications to make the order of the classifications match the expected order.

Example 3 includes the apparatus of example 1, wherein the sub sampler is to filter data points within the time series data to create a filtered data set, identify one or more properties of the data points in the filtered data set, and select data points as candidate samples based on corresponding ones of the one or more mathematical properties.

Example 4 includes the apparatus of example 1, wherein the sub sampler is to identify one or more properties of the data points in the time series data, and select data points as candidate samples based on the corresponding ones of the one or more properties.

Example 5 includes the apparatus of any one of examples 1 through 5, wherein the samples are collected by a sensor.

Example 6 includes the apparatus of example 1, wherein the accessed time series data includes a first number of samples and the one or more candidate samples includes a second number of samples less than the first number of samples.

Example 7 includes the apparatus of example 6, wherein the feature vector creator is to not generate feature vectors for samples that are not selected as the one or more candidate samples.

Example 8 includes the apparatus of example 1, further including a classified data provider to provide the classification to device functionality.

Example 9 includes a non-transitory machine-readable medium including instructions which, when executed, cause at least one processor to at least sub sample time series data to generate one or more candidate samples of interest within the time series data, generate feature vectors for respective ones of the one or more candidate samples of interest, attempt to classify the feature vectors based on a model; and in response to a classification of at least one of the feature vectors, associate the classification with at least one of the corresponding candidate sample or the corresponding sample.

Example 10 includes the non-transitory machine-readable medium of example 9, wherein the instructions, when executed, further cause at least one processor to identify that an order of classifications of the one or more candidate samples is not in an expected order, and in response to the identifying that the order of classifications is not in the expected order, remove one or more of the classifications to make the order of the classifications match the expected order.

Example 11 includes the non-transitory machine-readable medium of example 9, wherein the instructions cause the at least one processor to sub sample the time series data by filtering data points within the time series data to create a filtered data set, identifying one or more properties of the data points in the filtered data set, and selecting data points as candidate samples based on corresponding ones of the one or more properties.

Example 12 includes the non-transitory machine-readable medium of example 9, wherein the instructions cause the at least one processor to sub sample the time series data by identifying one or more properties of the data points in the time series data, and selecting data points as candidate samples based on the corresponding ones of the one or more properties.

Example 13 includes the non-transitory machine-readable medium of any one of examples 9 through 12, wherein the samples are collected by a sensor.

Example 14 includes the non-transitory machine-readable medium of example 9, wherein the time series data includes a first number of samples and the one or more candidate samples includes a second number of samples less than the first number of samples.

Example 15 includes the non-transitory machine-readable medium of example 14, wherein the instructions cause the at least one processor to not generate feature vectors for samples that are not selected as the one or more candidate samples.

Example 16 includes the non-transitory machine-readable medium of example 9, wherein the instructions, when executed, further cause the processor to provide the classification to device functionality.

Example 17 includes a method for analyzing time-series data, the method comprising sub sampling, by executing an instruction with at least one processor, time series data to generate one or more candidate samples of interest within the time series data, generating, by executing an instruction with the at least one processor, feature vectors for respective ones of the one or more candidate samples of interest, attempting to classify the feature vectors based on a model, and in response to a classification of one of the feature vectors, storing the classification in connection with the corresponding candidate sample.

Example 18 includes the method of example 17, further including identifying that an order of classifications of the one or more candidate samples is not in an expected order, and in response to the identifying that the order of classifications is not in the expected order, removing one or more of the classifications to make the order of the classifications match the expected order.

Example 19 includes the method of example 17, wherein the sub sampling of the time series data includes filtering data points within the time series data to create a filtered data set, identifying one or more properties of the data points in the filtered data set, and selecting data points as candidate samples based on corresponding ones of the one or more properties.

Example 20 includes the method of example 17, wherein the sub sampling of the time series data includes identifying one or more properties of the data points in the time series data, and selecting data points as candidate samples based on the corresponding ones of the one or more properties.

Example 21 includes the method of any one of examples 17 through 20, wherein the samples are collected by a sensor.

Example 22 includes the method of example 17, wherein the time series data includes a first number of samples and the one or more candidate samples includes a second number of samples less than the first number of samples.

Example 23 includes the method of example 22, further including not generating feature vectors for samples that are not selected as the one or more candidate samples.

Example 24 includes the method of example 17, further including providing the classification to a device functionality.

Example 25 includes an apparatus for analyzing time-series data, the apparatus comprising means for sub sampling time series data to identify one or more candidate samples of interest within the time series data, means for creating feature vectors corresponding to respective ones of the one or more candidate samples of interest, and means for attempting to classify the feature vectors based on a model, the attempting means to, in response to a classification of one of the feature vectors, store the classification in connection with the corresponding candidate sample in a memory.

Example 26 includes the apparatus of example 25, further including means for identifying that an order of classifications of the one or more candidate samples is not in an expected order, the identifying means to, in response to the identifying that the order of classifications is not in the expected order, remove one or more of the classifications to make the order of the classifications match the expected order.

Example 27 includes the apparatus of example 25, wherein the sub sampling means is to filter data points within the time series data to create a filtered data set, identify one or more properties of the data points in the filtered data set, and select data points as candidate samples based on corresponding ones of the one or more mathematical properties.

Example 28 includes the apparatus of example 25, wherein the sub sampling means is to identify one or more properties of the data points in the time series data, and select data points as candidate samples based on the corresponding ones of the one or more properties.

Example 29 includes the apparatus of any one of examples 25 through 28, further including sensing means for collecting the samples.

Example 30 includes the apparatus of example 25, wherein the accessed time series data includes a first number of samples and the one or more candidate samples includes a second number of samples less than the first number of samples.

Example 31 includes the apparatus of example 30, wherein the creating means is to not generate feature vectors for samples that are not selected as the one or more candidate samples.

Example 32 includes the apparatus of example 25, further including means for providing the classification to device functionality.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus for analyzing time-series data, the apparatus comprising:
    a sub sampler to sub sample time series data to identify one or more candidate samples of interest within the time series data, wherein the accessed time series data includes a first number of samples and the one or more candidate samples includes a second number of samples less than the first number of samples;
    a feature vector creator to create feature vectors corresponding to respective ones of the one or more candidate samples of interest; and
    a feature vector classifier to attempt to classify the feature vectors based on a model, the feature vector classifier to, in response to a classification of one of the feature vectors, store the classification in connection with the corresponding candidate sample in a memory.

2. The apparatus of claim 1, further including a spurious event remover to identifying that an order of classifications of the one or more candidate samples is not in an expected order, the spurious event remover to, in response to the identifying that the order of classifications is not in the expected order, remove one or more of the classifications to make the order of the classifications match the expected order.

3. The apparatus of claim 1, wherein the sub sampler is to filter data points within the time series data to create a filtered data set, identify one or more properties of the data points in the filtered data set, and select data points as candidate samples based on corresponding ones of the one or more mathematical properties.

4. The apparatus of claim 1, wherein the sub sampler is to identify one or more properties of the data points in the time series data, and select data points as candidate samples based on the corresponding ones of the one or more properties.

5. The apparatus of claim 1, wherein the samples are collected by a sensor.

6. The apparatus of claim 1, wherein the feature vector creator is to not generate feature vectors for samples that are not selected as the one or more candidate samples.

7. The apparatus of claim 1, further including a classified data provider to provide the classification to device functionality.

8. A non-transitory machine-readable medium including instructions which, when executed, cause at least one processor to at least:
    sub sample time series data to generate one or more candidate samples of interest within the time series data, wherein the time series data includes a first number of samples and the one or more candidate samples includes a second number of samples less than the first number of samples;
    generate feature vectors for respective ones of the one or more candidate samples of interest;
    attempt to classify the feature vectors based on a model; and
    in response to a classification of at least one of the feature vectors, associate the classification with at least one of the corresponding candidate sample or the corresponding sample.

9. The non-transitory machine-readable medium of claim 8, wherein the instructions, when executed, further cause at least one processor to:
    identify that an order of classifications of the one or more candidate samples is not in an expected order; and
    in response to the identifying that the order of classifications is not in the expected order, remove one or more of the classifications to make the order of the classifications match the expected order.

10. The non-transitory machine-readable medium of claim 8, wherein the instructions cause the at least one processor to sub sample the time series data by:
    filtering data points within the time series data to create a filtered data set;
    identifying one or more properties of the data points in the filtered data set; and
    selecting data points as candidate samples based on corresponding ones of the one or more properties.

11. The non-transitory machine-readable medium of claim 8, wherein the instructions cause the at least one processor to sub sample the time series data by:
    identifying one or more properties of the data points in the time series data; and
    selecting data points as candidate samples based on the corresponding ones of the one or more properties.

12. The non-transitory machine-readable medium of claim 8, wherein the samples are collected by a sensor.

13. The non-transitory machine-readable medium of claim 8, wherein the instructions cause the at least one processor to not generate feature vectors for samples that are not selected as the one or more candidate samples.

14. The non-transitory machine-readable medium of claim 8, wherein the instructions, when executed, further cause the processor to provide the classification to device functionality.

15. A method for analyzing time-series data, the method comprising:
   sub sampling, by executing an instruction with at least one processor, time series data to generate one or more candidate samples of interest within the time series data, wherein the time series data includes a first number of samples and the one or more candidate samples includes a second number of samples less than the first number of samples;
   generating, by executing an instruction with the at least one processor, feature vectors for respective ones of the one or more candidate samples of interest;
   attempting to classify the feature vectors based on a model; and
   in response to a classification of one of the feature vectors, storing the classification in connection with the corresponding candidate sample.

16. The method of claim 15, further including:
   identifying that an order of classifications of the one or more candidate samples is not in an expected order; and
   in response to the identifying that the order of classifications is not in the expected order, removing one or more of the classifications to make the order of the classifications match the expected order.

17. The method of claim 15, wherein the sub sampling of the time series data includes:
   filtering data points within the time series data to create a filtered data set; identifying one or more properties of the data points in the filtered data set; and
   selecting data points as candidate samples based on corresponding ones of the one or more properties.

18. The method of claim 15, wherein the sub sampling of the time series data includes:
   identifying one or more properties of the data points in the time series data; and
   selecting data points as candidate samples based on the corresponding ones of the one or more properties.

19. The method of claim 15, wherein the samples are collected by a sensor.

20. The method of claim 15, further including not generating feature vectors for samples that are not selected as the one or more candidate samples.

21. The method of claim 15, further including providing the classification to a device functionality.

* * * * *